US00PP12491P2

(12) United States Plant Patent

Olesen et al.

(10) Patent No.: US PP12,491 P2

(45) Date of Patent: Mar. 26, 2002

(54) SHRUB ROSE PLANT NAMED 'POULBICO'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/274,684

(22) Filed: Mar. 24, 1999

(51) Int. Cl.[7] ..... A01H 5/00

(52) U.S. Cl. ..... Plt./102

(58) Field of Search ..... Plt./101, 102, 107

(56) References Cited

PUBLICATIONS

Copy of EU 0357, published Aug. 2, 1996.*
Copy of EU 0607/95, filed Aug. 8, 1995.*
Copy of PBR Grant #5116 (cover sheet).*
UPOV–ROM, 2000/04, Plant Variety Database, GTI Jouve Retrieval Software, 3 citations for 'POULbico'.*

* cited by examiner

*Primary Examiner*—Howard J. Locker

(57) ABSTRACT

A new ground cover rose plant which has abundant, non-fading, red-purple and lavender-striped flowers, vigorous growth, and attractive foliage. This new and distinct variety has shown to be uniform and stable in the resulting generations from asexual propagation.

1 Drawing Sheet

SUMMARY OF THE INVENTION

The present invention constitutes a new and distinct variety of shrub rose plant which originated from a controlled crossing between an unnamed seedling (non-patented) and unnamed seedling (non-patented). The two parents were crossed and the resulting seeds were planted in a controlled environment.

The new variety is named 'POULbico'.

The new rose may be distinguished from its seed parent, an unnamed seedling, by the following combination of characteristics:

1. The seed parent is a floribunda rose with medium sized double flowers, while 'POULbico' is a shrub rose with single flowers.

2. The seed parent has deep pink, soft pink and white striped flowers. The pink colors are stronger than those of 'POULbico'. Additionally, 'POULbico' displays lavender stripes, where those of the seed parent are white.

The new variety may be distinguished from its pollen parent, an unnamed seedling, created by the same inventors, by the following combination of characteristics:

1. The pollen parent is a floribunda with pink flowers, while 'POULbico' is a shrub rose with striped flowers.

The objective of the hybridization of this rose variety for commercial greenhouse culture was to create a new and distinct variety with unique qualities, such as:

1. Uniform and abundant striped flowers;

2. Vigorous and compact growth;

3. Disease resistance and a low maintenance requirement in the lanscape.

This combination of qualities is not present in previously available commercial cultivars of this type and distinguish 'POULbico' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULbico' was selected by the inventors as a single plant from the progeny of the hybridization in the spring of 1987 as a single plant from the progeny of the aforementioned hybridization.

Asexual reproduction of 'POULbico' by cuttings and traditional budding was first done by L. Pernille and Mogens N. Olesen in August, 1987 in a nursery in Fredensborg, Denmark. This initial and other subsequent propagations conducted in controlled environments have demonstrated that the characteristics of 'POULbico' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULbico'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULbico', as observed in its growth in our field nursery in Jackson County, Oreg. Color references are made using The Royal Horticultural Society (London, England) Colour Chart, 1995, except where common terms of color are used.

For a comparison, several physical characteristics of the rose variety 'POULans', a rose variety from the same inventors described and illustrated in U.S. Plant Pat. No. 9,664 and issued on Oct. 22, 1996 compared to 'POULbico' in Chart 1.

CHART 1

| | 'POULbico' | 'POULans' |
|---|---|---|
| Petalage. | 5 to 7 petals. | 18 to 26 petals. |
| Petal color, upon opening, upper surface. | Red Group 53A with stripes of Red Group 55B and Red Group 56D. | Near Red Group 53A to 53B, changing to white at the base. |
| Flower bloom size. | 35 to 40 mm average diameter. | 45–55 mm average flower flower diameter. |

Classification:
*Botanical.*—*Rosa hybrida.*
*Commercial.*—Shrub.

FLOWER AND FLOWER BUD

Blooming habit: Recurrent.
Flower bud:
*Size.*—Upon opening, 18 mm–22 mm in length from base of receptacle to end of bud.
*Bud form.*—Short. Pointed ovoid.
*Bud color.*—As sepals unfold, Red Group 53A with areas of Red Group 56A and 56D and Yellow Group 10D. Red Group 53A to Red-Purple Group 59B with varigations/stripes of Red Group 54C, 55B, and 56D at ¼ opening.
*Sepals.*—Yellow-Green Group 146B. Weak foliaceous appendages. Stipitate glands are present in limited numbers on margins and outermost surfaces of sepals.
*Receptacle.*—Surface: Smooth. Shape: Urn-shaped. Size: Medium. 4 mm (h)×4 mm (w). Color: Yellow-Green Group 146B.
*Peduncle.*—Surface: With numerous stipitate glands. Length: 25 to 30 mm average length. Color: Yellow-Green Group 146C. Strength: Erect.
*Borne.*—Multiple buds per stem. Generally with 8 to 12 buds per flowering stem.
Flower bloom:
*Fragrance.*—Moderate wild rose scent. Sweet floral.
*Duration.*—The blooms have a duration on the plant of approximately 3 to 4 days. Petals fall cleanly away from plant.
*Size.*—Average flower diameter is 35–45 mm when open.
*Form.*—Shape of flower when viewed from the side: Upon opening, upper part: Flattened convex. Upon opening, lower part: Convex. Open flower, upper part: Flat to flattened convex. Open flower, lower part: Flattened convex.
*Petalage.*—Single. Average range: 5 to 7 petals under normal conditions with 2–3 petaloids.
Color:
*Upon opening, petals.*—Petals: Upper Surface: Red Group 53A with stripes/variegations of Red Gorup 55B and Red Group 56D. Reverse Side: Red Group 53A with variegations of Red Group 46A, 55B, 56A, and 56D. Some petals with midrib variegation of Red Group 56D — White Group 155C.
*Upon opening, basal petal spots.*—Outer Side: Yellow Group 4A. Inner Side: Yellow Group 9A–B.
*After opening, petals.*—Upper Surface: Red Group 53A–B with variegations of Red Group 55B and Red Group 56D. Reverse Side: Red Group 53A–B with variegations of Red Group 46A, 55B, 56A, and 56D.
*After opening, basal petal spots.*—Outer Side: Yellow Group 4B. Inner Side: Yellow Group 9B–C.
General tonality: Due to striped/variegated nature of the flower, general tonality not applicable. Red colors tend to finish more Red-Purple 59B to 59C and Red-Purple Group 62C–D.
Petals:
*Petal reflex.*—Limited to none.
*Petal edge.*—Uniform.
*Shape.*—Deltoid to round.
*Petaloids.*—Present. Quantity: 2–3.
*Thickness.*—Average.
*Arrangement.*—Informal.
Reproductive organs:
*Pollen.*—Color: Yellow Group 13A. Abundance: Above average abundance.
*Anthers.*—Size: Small to medium. Color, immature: Yellow Group 13B. Color, mature: Greyed-Orange Group 164C to Brown Group 200C. Abundance: Above average abundance.
*Filaments.*—Color: Yellow-Orange Group 15B.
*Stigmas.*—At same position as anthers. Color: Yellow-Green Group 145D.
*Styles.*—Color: Yellow-Green Group 145D.
*Hips.*—None observed.

PLANT

Plant growth: Vigorous, bushy, and irregular. When grown as a budded field grown plant on *R. multiflora* understock, the average height of the plant itself is 90 cm and the average width is 120 cm.
Stems:
*Color.*—Young wood: Yellow-Green Group 146C. Older wood: Yellow-Green Group 146C.
*Prickles.*—Incidence: Above average numbers of thorns. On upper portion of flowering stems numerous small prickles present. Size: Average length: 5 mm–6 mm. Color: Yellow-Green Group 145D, turning to Greyed-Yellow Group 162B. Shape: Deeply concave.
*Surface.*—Young wood: Smooth. Older wood: Smooth.
Plant foliage: Quantity of leaflets on normal leaves in middle of the stem: 5 leaflets.
*Leaf size.*—75–85 mm (l)×55–60 mm (w).
*Abundance.*—Average.
*Color.*—Upper Leaf Surface: Green Group 137A. Lower Leaf Surface: Green Group 138B. Juvenile foliage: Upper surface: Green Group 137A. Lower surface: Green Group 138B. Anthocyanin intonation: Location: Leaflet margins, undersides, veins, rachis, petiole, and stems of new shoots. Color: Greyed-Red Group 181A.
Plant leaves and leaflets:
*Stipules.*—Size: 14 mm–16 mm. Color: Green Group 137B. Stipitate glands: Present on margins.
*Petiole.*—Length: 20 mm–25 mm. Color: Green Group 137B. Underneath: With stipitate glands and small prickles. Margins: With stipitate glands.
*Rachis.*—Color: Green Group 137B. Underneath: With stipitate glands and small prickles. Margins: With stipitate glands.

*Leaflet*.—Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is moderately glossy. Lower side of leaflet is matte.

Disease resistance: Average resistance to mildew, black spot, and Botrytis under normal growing conditions in Jackson County, Oreg.

Winter hardiness: Winter hardy in Denmark and in Jackson County, Oreg.

We claim:

1. A new and distinct variety of rose plant of the shrub class, substantially as herein illustrated and described as a distinct and novel rose variety due to its abundant, striped flowers, vigorous and compact growth, disease resistance, and suitability for use in landscape.

* * * * *

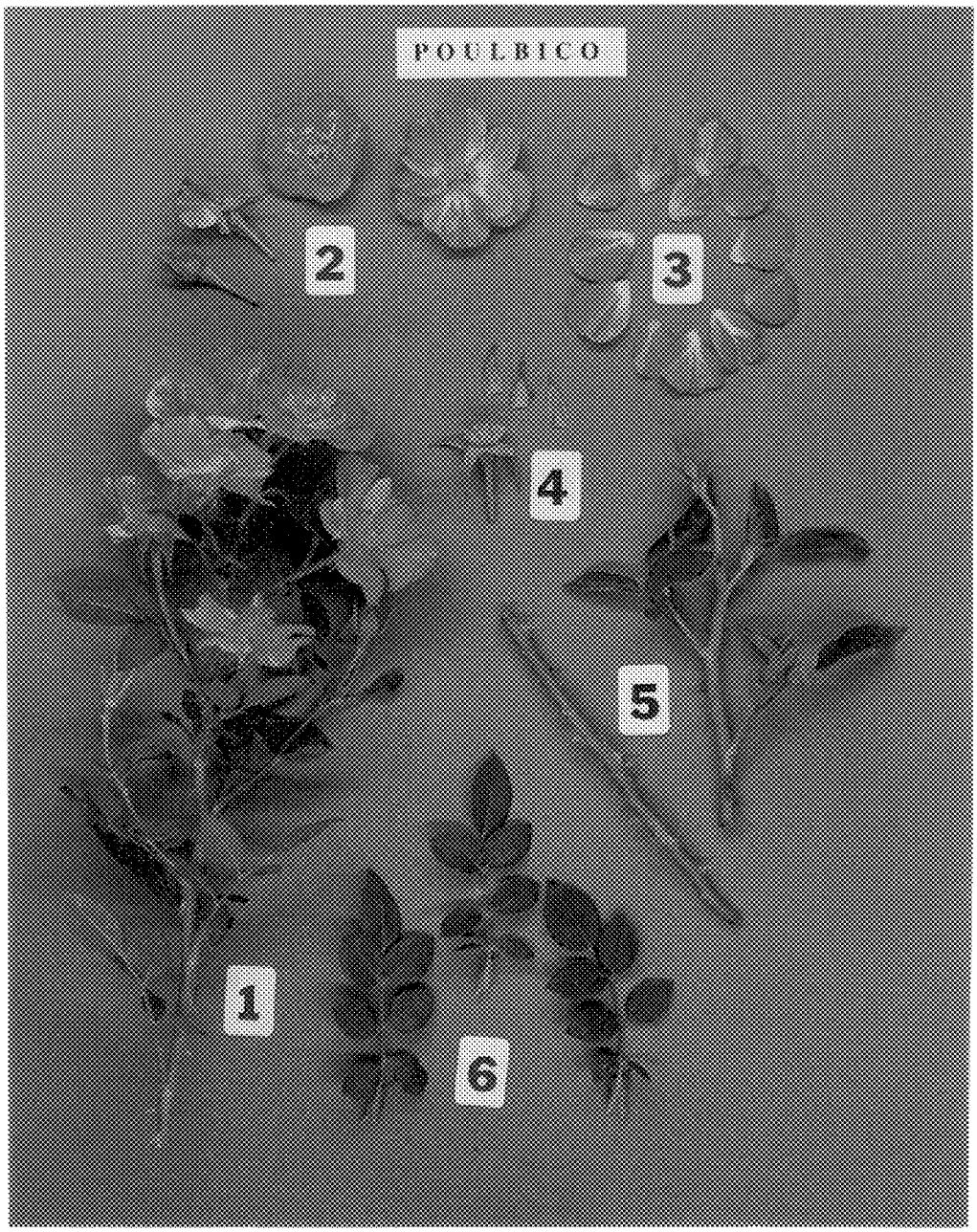
POULBICO
2
3
4
5
1
6